(12) United States Patent
Pillwein et al.

(10) Patent No.: US 10,589,450 B2
(45) Date of Patent: Mar. 17, 2020

(54) METHOD FOR DETERMINING A VALUE FOR THE DESCRIPTION OF THE COMPRESSION OF A MOLDABLE MATERIAL

(71) Applicant: ENGEL AUSTRIA GmbH, Schwertberg (AT)

(72) Inventors: Georg Pillwein, Linz (AT); Ruth Markut-Kohl, Schwertberg (AT)

(73) Assignee: Engel Austria GmbH, Schwetberg (AT)

( * ) Notice: Subject to any disclaimer, the term of this patent is extended or adjusted under 35 U.S.C. 154(b) by 299 days.

(21) Appl. No.: 15/149,459

(22) Filed: May 9, 2016

(65) Prior Publication Data

US 2016/0332342 A1 Nov. 17, 2016

(30) Foreign Application Priority Data

May 11, 2015 (AT) .............................. A 50383/2015

(51) Int. Cl.
*B29C 45/76* (2006.01)
*G01N 33/44* (2006.01)

(52) U.S. Cl.
CPC .......... *B29C 45/76* (2013.01); *B29C 45/7693* (2013.01); *G01N 33/44* (2013.01);
(Continued)

(58) Field of Classification Search
CPC ............................. B29C 45/76; B29C 45/7693
(Continued)

(56) References Cited

U.S. PATENT DOCUMENTS 2,770,011 A * 11/1956 Kelly .................. B29C 45/2806
249/79
3,137,750 A * 6/1964 Gringras ............. B29C 33/0055
264/257
(Continued)

FOREIGN PATENT DOCUMENTS

CN         1464832      12/2003
CN       101088738      12/2007
(Continued)

OTHER PUBLICATIONS

Machine translation of DE 102007030637 (Year: 2009).*
(Continued)

*Primary Examiner* — Robert C Dye
*Assistant Examiner* — Russell E Sparks
(74) *Attorney, Agent, or Firm* — Wenderoth, Lind & Ponack, L.L.P.

(57) ABSTRACT

In a method for determining at least one parameter for the description of the compression behavior of a material processed in a molding machine, at least a part of the processed material is introduced into a mold cavity via a distribution system and a gate, and the processed material solidifies in the mold cavity. A compression test is performed in which a volume storing the material is modified and a measurement of the resulting pressure modification is conducted or a pressure applied onto the material is modified and a measurement of the resulting modification of the volume is conducted. A parameter for the description of the compression behavior is calculated based on the result of the compression test by using a mathematical model. The compression test is conducted when the gate is at least substantially solidified or when the hot runner is closed.

14 Claims, 5 Drawing Sheets

(52) U.S. Cl.
 CPC .............. *B29C 2945/76103* (2013.01); *B29C 2945/76107* (2013.01); *B29C 2945/76287* (2013.01)

(58) Field of Classification Search
 USPC ........................................................ 264/40.1
 See application file for complete search history.

(56) References Cited

U.S. PATENT DOCUMENTS

| | | | |
|---|---|---|---|
| 4,816,197 A * | 3/1989 | Nunn | B29C 45/76 264/40.1 |
| 5,030,395 A * | 7/1991 | Kamiguchi | B29C 45/76 264/328.13 |
| 5,108,689 A | 4/1992 | Uehara et al. | |
| 5,178,805 A | 1/1993 | Yokota | |
| 5,500,166 A | 3/1996 | Sasaki et al. | |
| 5,716,560 A | 2/1998 | Heuchert et al. | |
| 5,772,932 A * | 6/1998 | Kamiguchi | B29C 45/561 264/328.7 |
| 6,244,848 B1 * | 6/2001 | Ito | B29C 45/77 425/149 |
| 6,616,868 B1 | 9/2003 | Gotoh et al. | |
| 6,705,725 B2 | 3/2004 | Gotoh et al. | |
| 7,323,125 B2 | 1/2008 | Uwaji et al. | |
| 7,559,762 B2 | 7/2009 | Dewar et al. | |
| 7,766,647 B2 | 8/2010 | Dewar et al. | |
| 9,739,694 B2 * | 8/2017 | Amanullah | C09K 8/03 |
| 2003/0116876 A1 | 6/2003 | Wobbe | |
| 2003/0201555 A1 | 10/2003 | Gotoh et al. | |
| 2004/0140579 A1 | 7/2004 | Uwaji et al. | |
| 2007/0292557 A1 | 12/2007 | Dewar et al. | |
| 2009/0045537 A1 | 2/2009 | Cheng et al. | |
| 2009/0274787 A1 | 11/2009 | Dewar et al. | |
| 2011/0254198 A1 | 10/2011 | Abd Elhamid et al. | |

FOREIGN PATENT DOCUMENTS

| | | | |
|---|---|---|---|
| DE | 102007030637 A1 * | 1/2009 | ............ B29C 45/20 |
| EP | 0 478 788 | 4/1992 | |
| EP | 1 106 326 | 6/2001 | |
| JP | 9-187834 | 7/1997 | |
| JP | 11188763 | 7/1999 | |
| KR | 96-7282 | 5/1996 | |

OTHER PUBLICATIONS

Foster III, G. N., Waldman, N., Griskey, R. G. (1966). Pressure-Volume-Temperature Behavior of Polypropylene. Polymer and Engineering Science, pp. 131-134. (Year: 1966).*

Search Report dated Feb. 26, 2018 in Chinese Patent Application No. 201610656780.4.

* cited by examiner

METHOD FOR DETERMINING A VALUE FOR THE DESCRIPTION OF THE COMPRESSION OF A MOLDABLE MATERIAL

BACKGROUND OF THE INVENTION

The material prepared in a material storage space is introduced in a mold cavity, for example arranged in a molding tool, via a gating system formed by a distribution system and a gate. The material solidifies in the mold cavity. The "gate" (i.e., "ingate" or "inlet port") is that part of a gating system which connects the molded part (in the case of an injection molding machine also called the injection molded part) formed by the solidified material in the mold cavity with the distribution system.

There are different parameters for the description of the compression behavior of a compressible material, for example the compression modulus K which is exemplarily discussed in the following. However, the invention can also be realized with other parameters (such as the compressibility).

The compression modulus K of a material describes which all-sided pressure modification is necessary in order to cause a determined modification of the volume of the material. It is defined as:

$$K = -V \frac{dp}{dV} \quad \text{(Equation 1)}$$

V . . . volume
dp . . . (infinitesimal) pressure modification
dV . . . (infinitesimal) volume modification
dV/V . . . relative volume modification In the following, plastic melt is discussed as an example for the processed material, and an injection molding machine is discussed as an example for a molding machine. The invention is not limited to one of these examples.

Pressure and volume of a plastic melt are two of the most important physical parameters when processing plastics in an injection molding process. Therefore, the compression modulus also has an enormous significance for the injection molding. The force applied onto the injection piston and the thus emerging pressure have the primary function to get the melt flowing and to thereby fill a molding tool cavity. By the required pressure, a volume reduction corresponding to the compression modulus occurs. The temporal modification of the screw position and the thereof calculated volume thus contains proportions which correspond to the volume flow in the cavity and proportions which have their origin in the compression of the melt. In order to detect and to distinguish these proportions, the knowledge of the compression modulus as well as the actually present melt volume is necessary.

A generic method is disclosed in the EP 0 478 788 A1 (Komatsu). In this Komatsu reference, the execution of a compression test is described with reference to therein indicated FIG. 7. The compression test is executed when the machine nozzle is closed at the position 30 and thereby considers the volume of the screw vestibule and the material designated with reference sign 6.

SUMMARY OF THE INVENTION

The object of the invention is to provide a method which allows it more exactly than the prior art to determine a parameter for the description of the compression behavior of a material processed in a molding machine, and to provide an injection molding machine in which the thus determined data are saved.

By the invention, it is possible that the whole dead volume of a molding machine is considered when determining the at least one parameter for the description of the compression behavior, because the material storage space remains unclosed during the compression test. In the Komatsu reference based on the closed cylinder, only the dead volume—anyway known based on the machine construction—in the cylinder is considered. The gating/distribution system provided in the molding tool is not considered.

In an exemplary manner, the invention is explained in the following based on an injection molding machine which comprises a plasticizing screw arranged in a plasticizing cylinder and functioning as a piston. The method, however, is generally applicable with a molding machine with a material storage space for processing and gathering the processed materials and is in particular also applicable to an injection molding machine in which a piston is arranged in a material storage space.

In the prior art, the pressure of the plastic melt is usually measured directly or indirectly by suitable sensors. Usually, the volume is calculated from the measured position of the screw or the injection piston and the known cross sectional area. This calculated volume is usually not identical with the actual melt volume. The additional melt volume which is existing in the screw vestibule (including flange, nozzle, . . . ) and in the gating system respectively, is not considered or even displayed in injection molding machines according to the prior art. On the basis of tolerances and possibly unknown dimensions of, for example, the hot runner system, the melt volume is in many cases a priori not exactly known.

Thus, the volume V is composed of different proportions:

$$V = V_{screw\_position} + V_{nozzle} + V_{flange} + V_{hot\_runner} + \ldots \quad \text{(Equation 2)}$$

At first, for the present invention only, the distinction between the proportions calculated based on the screw position and the remaining proportions are relevant. The remaining proportions (not accessible by the screw movement) are thus summarized under the term dead volume ($V_{dead}$).

$$V = V_{screw\_position} + V_{dead} \quad \text{(Equation 3)}$$

Also for the compression modulus—dependent of the type of the raw material and parameters like pressure and temperature—these values are usually not known exactly enough.

In general, the compression modulus itself is pressure-dependent, this means K=K(p). The pressure dependency of the compression modulus of plastics in many cases can be well modeled by a linear relation in the form $$K(p) = K_0 + K_1 p \quad \text{(Equation 4)}$$

with constant parameters $K_0$ and $K_1$. Of course other models can also be used. By plugging the linear model in the definition of the compression modulus and by rearranging, the following differential equation is obtained:

$$\frac{dV}{V} = -\frac{dp}{K_0 + K_1 p} \quad \text{(Equation 5)}$$

Integration results in $$\ln V = -\frac{1}{K_1}\ln\left(\frac{K_0 + K_1 p}{K_0}\right) + c \quad \text{(Equation 6)}$$

respectively $$V = e^c e^{-\frac{1}{K_1}\ln\left(\frac{K_0 + K_1 p}{K_0}\right)} \quad \text{(Equation 7)}$$

Plugging in the boundary condition $V(p=0)=V_0$ results in $$V(p) = V_0 e^{-\frac{1}{K_1}\ln\left(\frac{K_0 + K_1 p}{K_0}\right)} \quad \text{(Equation 8)}$$

These equations are exemplary and are modified correspondingly under deviating model hypotheses for the pressure dependency of the compression modulus. For a pressure-independent compression modulus ($\lim K_1 \to 0$) it simplifies for example to $$V(p) = V_0 e^{-\frac{p}{K_0}} \quad \text{(Equation 9)}$$

Based on the example of equation 8 the aim is the determination of the parameters $V_0$, $K_0$, $K_1$. In order to obtain data from which these values can be calculated either a modification of the screw position and a measurement of the resulting pressure modification or a modification of the applied pressure and a measurement of the modification of the screw position is necessary. Such a procedure, in which either the volume (the screw position) or the pressure varies and values are acquired metrological, are designated in the following as a compression test.

From the measured value pairs of the screw position and the pressure $V_S$–p, thus from such a single compression test, basically already all three values can be determined. Practice shows that these problems are difficult to solve numerically. There are numerous combinations of parameters which very well describe the data but are far away from the actual parameter values. Already little measurement noise thus hampers an exact determination of the parameters in practice.

In order to obtain values for the compression modulus and the dead volume, thus preferably at least two compression tests are executed under different boundary conditions.

EXAMPLE

Two compression tests are executed with two different melt volumes and therefore different screw positions S1 & S2. The result are for example pressure values $p_i$ and the corresponding volume values $V_{S1,i}$ und $V_{S2,i}$ calculated from the respective screw position. The derivatives $dp/dV_{S1}$ respectively $dp/dV_{S2}$ can be determined numerically from the value pairs $(V_{S1,i}|p_i)$ respectively $(V_{S2,i}|p_i)$. Under the assumption that the compression modulus of the material is the same in both cases, the following applies:

$$-(V_{dead}(p_i) + V_{S1,i})\frac{dp}{dV}\bigg|_{V=V_{S1,i}} = \quad \text{(Equation 10)}$$
$$-(V_{dead}(p_i) + V_{S2,i})\frac{dp}{dV}\bigg|_{V=V_{S2,i}}$$

Therefore, when having pressure $p_i$ the dead volume $V_{dead}$ can be calculated as $$V_{dead}(p_i) = \frac{V_{S2,i}\frac{dp}{dV}\big|_{V=V_{S2,i}} - V_{S1,i}\frac{dp}{dV}\big|_{V=V_{S1,i}}}{\frac{dp}{dV}\big|_{V=V_{S1,i}} - \frac{dp}{dV}\big|_{V=V_{S2,i}}} \quad \text{(Equation 11)}$$

As herein assumed, the dead volume itself can also be pressure-dependent in general. Modifications of the dead volume result from the deformation of the mechanical components under pressure (stretch of the cylinder, compression of the piston/screw, of the drive train . . . ). By the evaluation of equation 11 under different pressure levels, the pressure dependency can be determined.

As $V_{dead}(p_i)$ is now known, the compression modulus $K(p_i)$ can be calculated at a specific pressure $p_i$ according to the definition of the compression modulus.

$$K(p_i) = -(V_{S1,i} + V_{Tot}(p_i))\frac{dp}{dV}\bigg|_{V=V_{S1,i}} \quad \text{(Equation 12)}$$

From the values $K(p_i)$ at at least two different pressure values $p_i$, the parameters $K_0$ and $K_1$ can be calculated subsequently, these parameters are describing the pressure dependency $K(p)$ model-based or the parameters of another model.

In a similar manner it is possible to generate a model for the pressure dependency of the dead volume from the values $V_{dead}(p_i)$. In a first approximation for example the linear formulation $V_{dead}(p)=V_{dead,0}+\kappa_{mech}p$ could be chosen.

These determined values for the compression modulus and for the dead volume respectively can be displayed on a screen of the machine or can be recorded or documented in a control.

By the variation of other influencing factors (for example the temperature of the processed material or the modification rate of the pressure or the volume during the compression test) and repeated determination of the compression modulus and/or the dead volume, of course also the relation to the influence factors can be determined and can be described by corresponding models if necessary From the combination of the pressure dependency and the temperature dependency of the compression modulus, subsequently the behavior V(p,T) as a parameter of the material can be determined. If the weight of a defined volume (for example by injection) is additionally determined, then the behavior of the specific volume V(p,T) can be determined and displayed.

Both compression tests for determining the dead volume can be movement sequences which are part of a "normal injection cycle", additional movement sequences which are integrated into a normal injection cycle or movement sequences especially for this purpose which are conducted fully apart from the normal production process. Both of the first variants have the advantage that the determination can take place directly in the running production process under the prevalent conditions, whereas in the third variant the configuration of the movement sequence is more flexible. Examples for suitable movements in the normal injection cycle are the pressure reduction at the end of the holding pressure phase and/or the pressure relief after the dosing operation.

As the dead volume can be assumed constant in a specific arrangement (machine+molding tool) subsequently modifications of the compression modulus can be determined from single compression tests. Such compression tests for the repeated determination of the compression modulus can again be movements which are part of a "normal injection cycle", additional movement sequences which are integrated into a normal injection cycle or movement sequences especially for this purpose which are conducted fully apart from the normal production process. Examples for suitable movements in the normal injection cycle are the pressure reduction at the end of the holding pressure phase or the pressure relief after the dosing operation. In an ideal case (but not necessarily) no more melt flow into the cavity takes place at the time of the compression test. This can be ensured by closing mechanisms if corresponding closing mechanisms are provided in the machine nozzle or hot runner nozzle. If no closing is possible, then the whole non-solidified area of the melt connected with the melt in the screw vestibule is included in the determination of the dead volume and/or the compression modulus.

Preferably, the at least one compression test is made in the form of a pressure drop.

The main aspect of the present invention is that the whole dead volume is considered in the calculation of the at least one parameter for the description of the compression behavior. An important side aspect of the present invention is also for what purpose these parameters for the description of the compression behavior are applied. Therefore, protection is also sought for a method for operating a molding machine on the basis of at least one parameter (this parameter can be saved or can have been calculated in a method according to the invention) for the description of a compression behavior. Therefore, on the basis of this parameter a realistic injection volume and/or a realistic injection volume flow is calculated, a decompression lift is calculated, a dwell time of the melt in the molding machine is calculated, a pressure regulator is parameterized, a pressure dependency of the compression behavior is determined, a temperature of the melt is determined, the velocity of the plasticizing screw is controlled or regulated, so that a predetermined filling volume flow is reached, and/or a material characteristic of the melt is determined. Such a material characteristic for example is the composition, the phase state, the viscoelasticity, the solids content, the proportion of low-molecular substances or the chemical modifications of the polymer structure.

Particulars of this aspect are described in the following, wherein the concrete possible applications of the parameters for the description of the compression behavior are explained in more detail. The first four described application possibilities refer to the volume and the volume flows.

Calculation of a Realistic Injection Volume:

With the equation 13 the volume reduction in consequence of a compression starting from $V_0$ under a specific pressure p can be calculated.

$$\Delta V(p) = V_0 - V(p) = V_0 \left[ 1 - \left( \frac{K_0 + K_1 p}{K_0} \right)^{-\frac{1}{K_1}} \right] \quad \text{(Equation 13)}$$

If the constants $V_0$, $K_0$ and $K_1$ are known, then the volume proportion $\Delta V(p)$ which emerges by compression can be calculated approximately.

The dosing volume $V_D$ measured at the machine is calculated from the measured screw position and the screw diameter. The modification of this measured dosing volume during the injection cycle, for example during an injection process, is composed of several proportions.

$$\Delta V_D = V_{D,0} - V_D = \Delta V(p) + \Delta V_{fill} + \Delta V_{leak} \quad \text{(Equation 14)}$$

$V_{D,0}$ here designates a dosing volume at the beginning of the injection and $V_D$ the current value of the dosing volume during the injection process. The proportion $\Delta V_{fill}$ corresponds to the actual modification of the volume which occurs at the flow front. The proportion $\Delta V_{leak}$ designates the reduction of the volume due to the loss of material by leakages (for example by the non-return valve) and is neglected for the moment, because it is usually irrelevant in the injection phase (at least when the non-return valve is closed). The actually injected volume would be in this case $$\Delta V_{fill} = \Delta V_D - \Delta V(p) \quad \text{(Equation 15)}$$

It is reduced compared to volume difference calculated from the modification of the screw position by the compression proportion $\Delta V(p)$. Conversely, a hypothetical dosing volume $V_D'$ can be calculated which quasi only contains the filling proportions.

$$V_D' = V_{D,0} - \Delta V_{fill} = V_D + \Delta V(p) \quad \text{(Equation 16)}$$

Hence, the following equation 17 results therefrom:

$$V_D' = V_D + V_0 \left[ 1 - \left( \frac{K_0 + K_1 p}{K_0} \right)^{-\frac{1}{K_1}} \right] \quad \text{for } K_1 \neq 0 \quad \text{(Equation 17)}$$

$$V_D' = V_D + V_0 \left( 1 - e^{-\frac{p}{K_0}} \right) \quad \text{for } K_1 = 0$$

Here, the assumption was made that the pressure is constant in the whole volume. In general, this assumption is sufficiently fulfilled only in the screw vestibule. For more exact results, it is in some circumstances appropriate to make assumptions by a pressure distribution p(V) in the melt and to integrate the above formula by the melt volume.

$$V_D' = V_D + \int_0^V \left[ 1 - \left( \frac{K_0 + K_1 p(V)}{K_0} \right)^{-\frac{1}{K_1}} \right] dV \quad \text{(Equation 18)}$$

The negative time derivation of $V_D'$ then corresponds to the actual filling volume flow with compression proportions. This calculated value can be used for example in order to regulate the screw velocity in such a way that a desired filling volume flow emerges.

Calculation of the Decompression Lift:

Before and/or after the dosing of the material, it is usual to relieve the melt pressure by a retraction of the screw (corresponds to the decompression or a compression relief). The necessary decompression lift correlates with the compression modulus and the melt volume. Given a pressure p with the already indicated equation $$\Delta V(p) = V_0 \left[ 1 - \left( \frac{K_0 + K_1 p}{K_0} \right)^{-\frac{1}{K_1}} \right] \quad \text{(Equation 19)}$$

the at least necessary decompression lift can be directly determined. The decompression lift is thus calculated by the knowledge of K(p) from the equation 19 in advance and not (fully) determined from the pressure progression during the decompression in the current injection cycle. If the value set by the operator is less than the value calculated in advance, then the control can issue a warning to the operator. The determined value can also be suggested by the control or automatically adjusted.

It has also appeared that after a decompression, material flows from the helical mounts into the screw vestibule and can lead again to a pressure build-up. The actually necessary decompression lift is therefore often a little higher than calculated by the above formula. Such a pressure build-up can be detected by the control and can be compensated for by an automatic increase of the decompression lift. In an alternative, the operator can be called to attention by a warning or a proposal. It is also possible to multiply the value determined from a formula with a sufficient safety factor. Such a safety factor can also be dependent from the used screw geometry and from the material type.

Dwell Time Calculation:

For the raw material (in particular for transparent polymers) the dwell time of the melt at high temperatures is of a great importance. The dwell time results from the material throughput and the whole melt volume (including the melt volume in the helical mounts). The melt volume in the helical mounts $V_{helic}$ can derive from the screw geometry and can be saved in the machine. At a known compression modulus and a known dead volume, the actually injected amount $V_{inject}$ and thereby the actual material throughput $V_{inject}/t_{cycle}$ can be calculated more exactly. Moreover, the calculated dead volume $V_{dead}$ can be included into the calculation of the dwell time. Therefore, the dwell time can be calculated more exactly than without the knowledge of the these values.

$$t_{dwell} = \frac{t_{cycle}}{V_{inject}}(V_{helic} + V_{dead} + V_D)$$ (Equation 20)

The dwell time can be displayed in the control and a warning can be displayed on the basis of limit values for different materials, if the recommended or permitted dwell time is exceeded.

Use of Pressure Regulator or Pressure Limit Regulator:

The values of the compression modulus and the dead volume can be used in order to better parameterize the pressure regulator or the pressure limit regulator. The maximally useful regulator amplification for example can be derived from these values. Also the known relation V(p) can be used for a pre-control (for example at a holding pressure control). Here knowledge of the separated values of K and V is not absolutely necessary, but under circumstances already the knowledge of the relation K/V is sufficient.

The following three described application possibilities refer to the material.

Dependencies K(p), K(T):

The determination of the pressure dependency of the compression modulus has been described already. As previously described, this dependency can be well described by linear relation:

$$K(p)=K_0+K_1 p$$ (Equation 21)

Also the values do not have to be determined in the machine, but can originate from the literature, from pvT date or from other sources.

The dependency of the compression modulus from the temperature can be determined by compression tests at differently adjusted cylinder temperatures.

It is sufficient to specify the dead volume at only one temperature. At further temperature values one compression test is sufficient to determine the modification of the compression modulus. The temperature dependency of the compression modulus can be approximately described for example by a linear formulation.

$$K(T)=K_0+K_T T$$ (Equation 22)

In order to determine the parameters $K_0$ and $K_T$, two compression tests at two different temperatures are sufficient under this assumption. It is of course possible to use other models or to determine the compression modulus at a plurality of temperatures and to save the value pairs in a table. In an ideal case, it can be ensured by a sufficient waiting period that at the compression tests a sufficiently homogenous temperature distribution is present in the melt. Also, the values do not have to be determined in the machine, but can originate from the literature, from pvT date or from other sources.

Determination of the Melt Temperature:

Conversely, at a known relation K(T), by measuring the compression modulus, it is possible to get in one compression test a conclusion to the actual temperature of the melt. This is of a particular advantage because the melt temperature is difficult to access for a measurement and requires expensive, complex and sensitive sensor technology. It is to be noted that the absolute value of the melt temperature is often not that important as relative modifications which can be observed directly from the determined compression modulus or from the ratio dp/dV without having to know the exact relation K(T). In order to keep the melt temperature constant, it would be sufficient under apart from that constant boundary conditions to keep the measured compression modulus or the value dp/dV constant. This could be used for example for the regulation of the melt temperature. In this regard, it is to be noted that the modification of the pressure and/or the volume of the melt can be effected by a movable molding tool element such as a core pull or an ejector.

Dependency on the Basis of the Loading Velocity—Detailed Determination of the Material Characteristics:

If conducting compression tests with different loading velocities, if necessary at differently adjusted cylinder temperatures (for example two velocities for each temperature) then the (viscoelastic) characteristics can be distinguished. The thus determined material parameters can serve as input data for the simulation of injection (sub-) processes. Moreover, the data can be used for the material identification and can be subsequently used:

for checking, whether the correct/intended material is utilized in the production or whether this material corresponds to the predetermined quality criteria (which can be predetermined by the operator). The quality of the material can also be gathered (recorded) by the quality management.

in order to support the operator when adjusting the plasticizing process (for example dosing velocity, minimum/maximum lift, cylinder temperature, etc.).

Material Characterization—Composition and Phase State:

The compression modulus is a material parameter which depends from the characteristics of the material in the considered volume. This material can consist of several components. The determined values for $K_0$, $K_1$ and/or the progress of K(p) reflect a mixture of characteristics of all components of the material in the considered volume. This material can contain, besides a polymer melt (possible is also metal or glass), further gaseous, liquid, supercritical and/or solid components. These components can be other materials (for example glass, carbon fiber, filling materials, low-molecular substances like water, nitrogen, etc., natural materials like talc, wood, etc., ceramic powder or metal powder), additives (for example pigments, masterbatch, etc.), other polymers (for example in polymer blends or copolymers) and/or degradation products, transformation products and formation products of the polymer melt. The components can be present in a solved state and/or as separated pure phases and/or mixing phases.

The values $K_0$, $K_1$ and the progress K(p) are compared either with the previously measured values (of the same injection cycle or of the previous injection cycle) or with values saved in the machine for the raw material, for the raw material type or for the process. From the values $K_0$, $K_1$ and from the progress K(p) as well as from their modifications the following can be concluded:

- The solid content in the melt. Example: Polypropylene (PP) with or without carbon fibers. More details can be seen in FIG. 6.
- The proportions of low-molecular substances in the polymer melt solvent or polymer melt mixture. Example: Detection of supercritical fluid bubbles, for example nitrogen bubbles when physically foaming. More details can be seen in FIG. 7.
- The modification of the raw material by chemical degradation reactions, transformation reactions and formation reactions of the polymer structure (for example also in a combination with the dwell time or the moisture content).
- The modifications in the material. In other words, it can be recognized whether the correct/intended material is utilized in the production or whether this material corresponds to the predetermined quality criteria (which can be predetermined by the operator). The quality of the material can also be collected by the quality management.

DETAILED DESCRIPTION OF THE INVENTION

Figure 1:
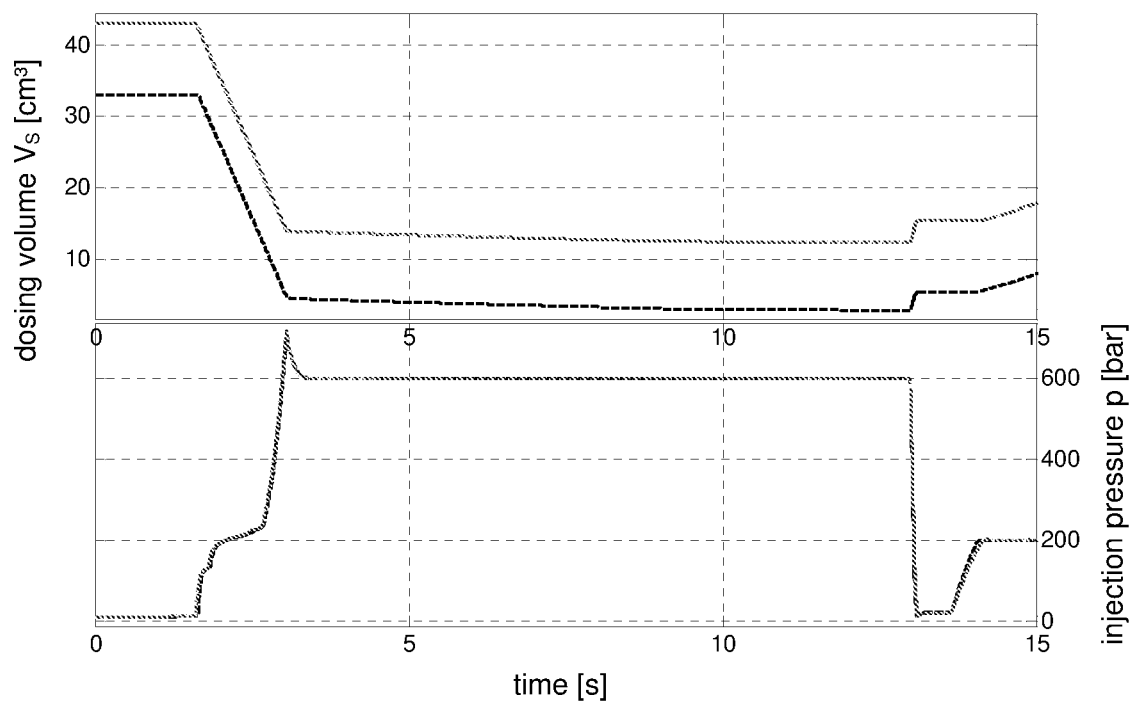
FIGS. 1 to 3 are graphs illustrating the performance of a first embodiment of the invention.

FIG. 1 shows the progress of the dosing volume and the injection pressure in two injection cycles with different initial dosing volumes.

Figure 2:
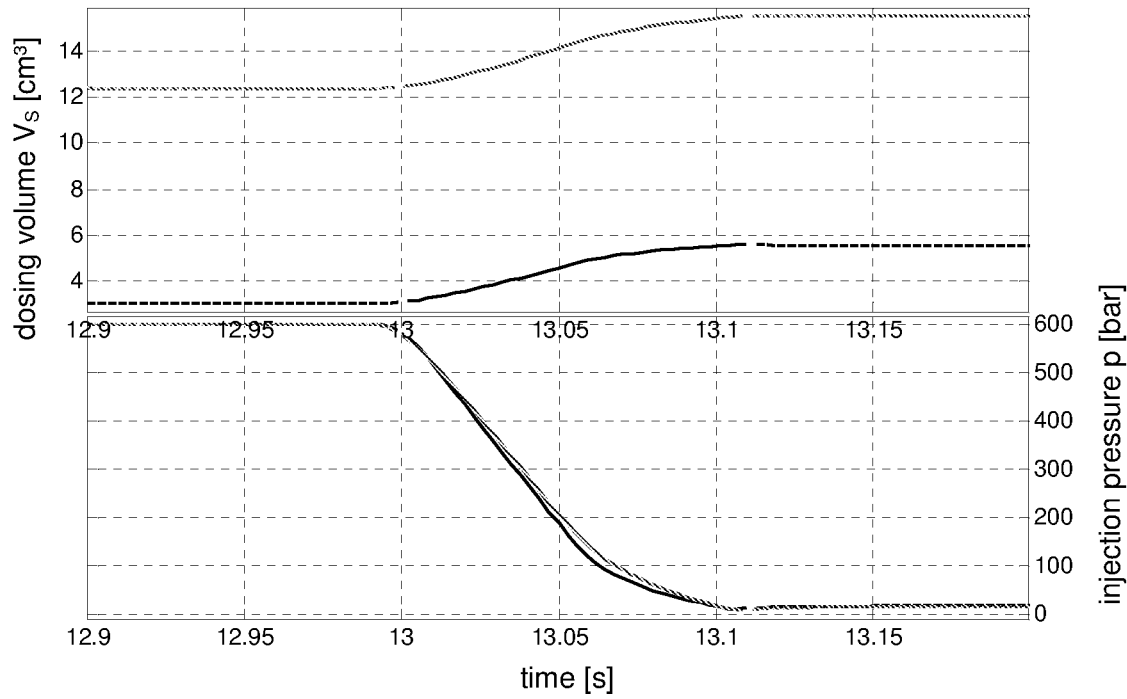

FIG. 2 shows an enlarged detail of FIG. 1. This represents the progress of the dosing volume and the injection pressure in the holding pressure reduction phase.

Figure 3:
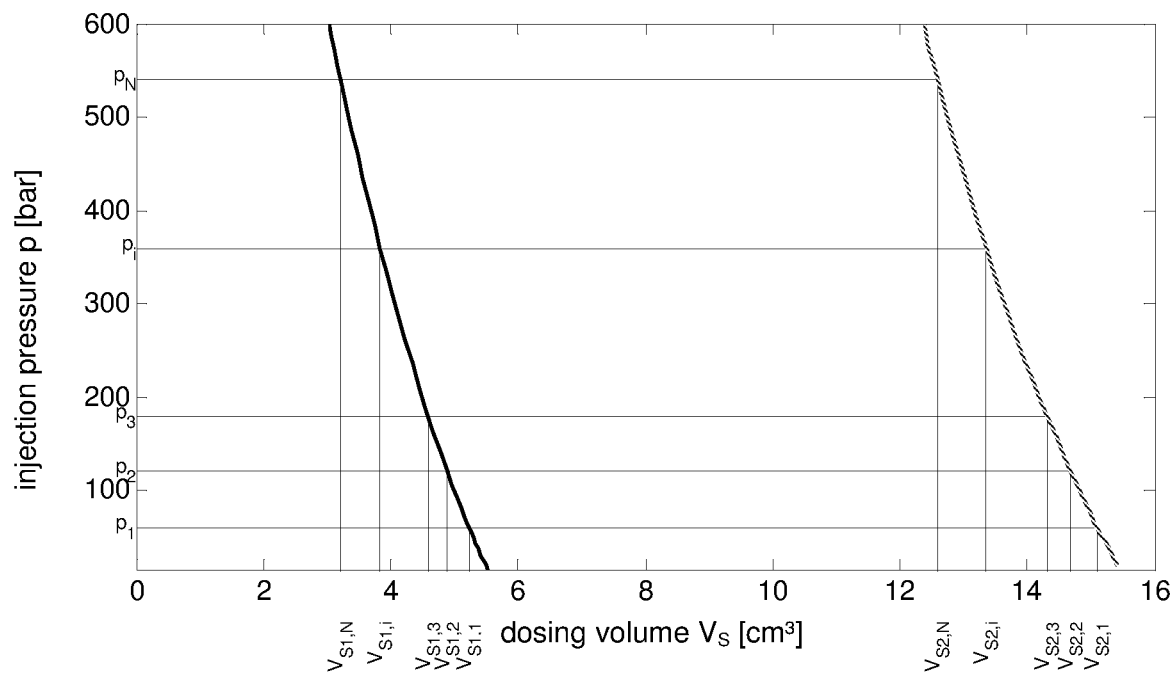

FIG. 3 shows the progress of the injection pressure over the dosing volume during the holding pressure reduction of FIGS. 1 and 2. The value pairs $V_{S1,i}|p_i$ and $V_{S2,i}|p_i$, respectively, are indicated.

The holding pressure reduction phase serves as the compression test. The modification of the dosing volume is reached by dosing different amounts of melt in two injection cycles independent from each other. During the holding pressure reduction phase, the value pairs $V_S$ and p are each recorded.

Figure 4:
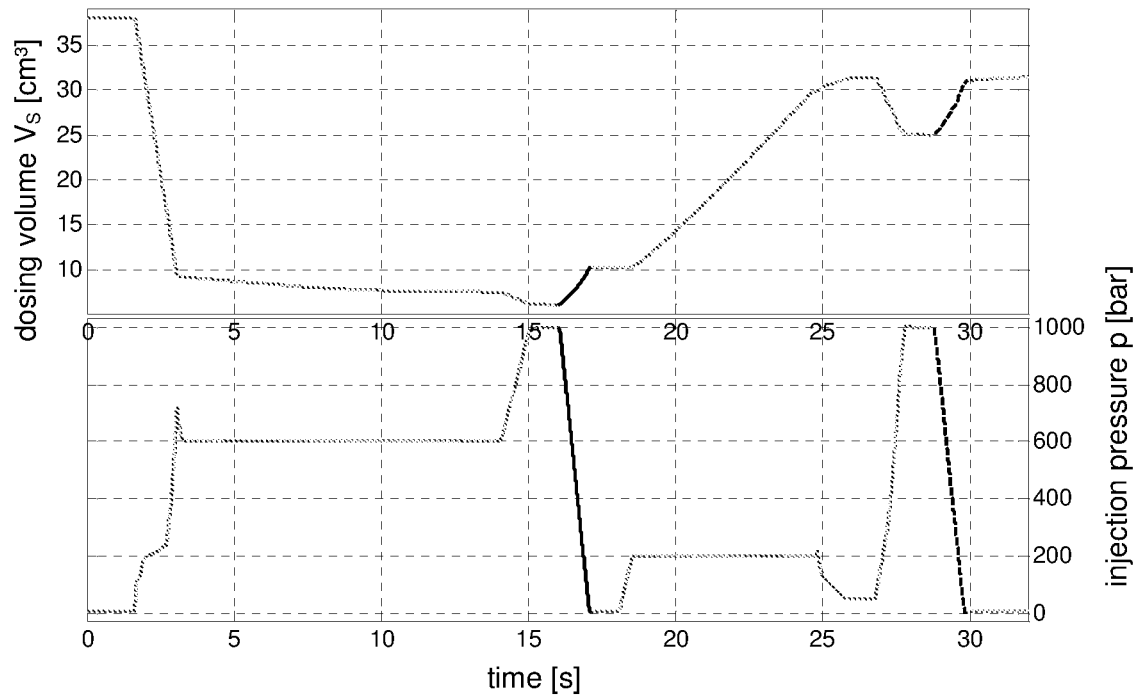
FIGS. 4 and 5 are graphs illustrating the performance of a second embodiment of the invention.

FIG. 4 shows two compression tests in an injection cycle. Compression test 1: after the holding pressure phase (drawn through line). Compression test 2: after the dosing phase (broken line). The rest of the progress of the volume and the pressure is indicated as a dotted line.

Figure 5:
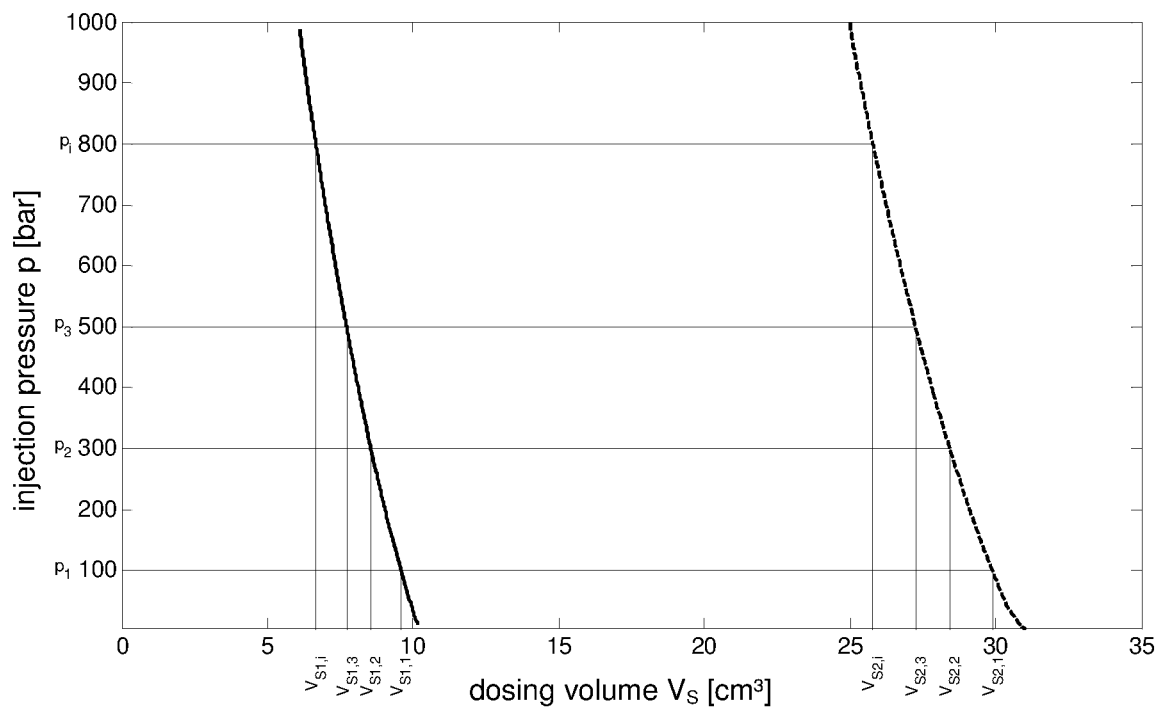
Figure 6:
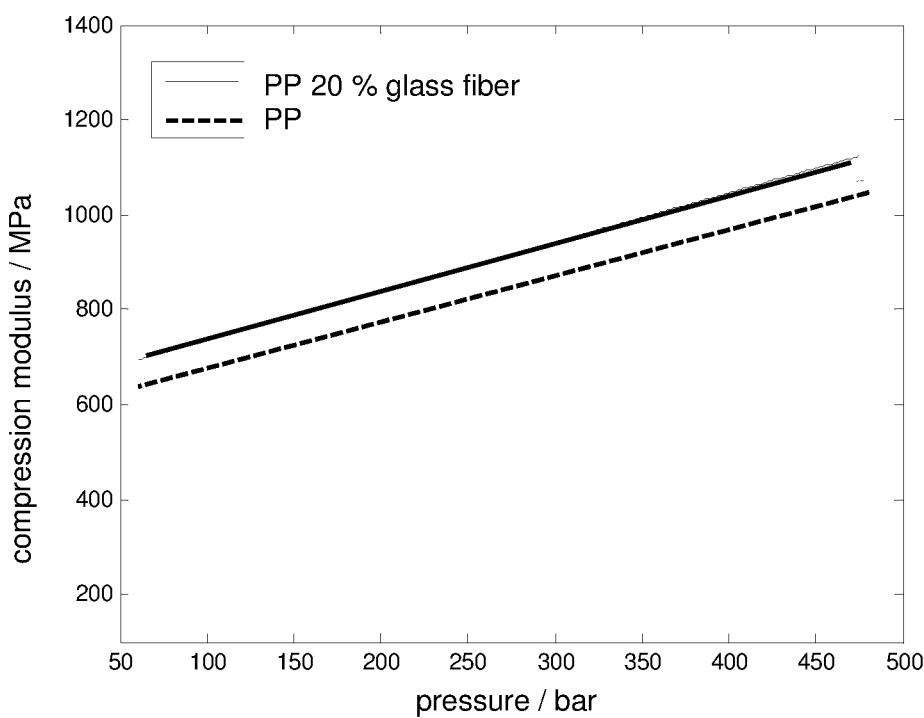
FIGS. 6 and 7 are graphs illustrating a conclusion reached from the calculated compression behavior to characteristics of the melt.
Figure 7:
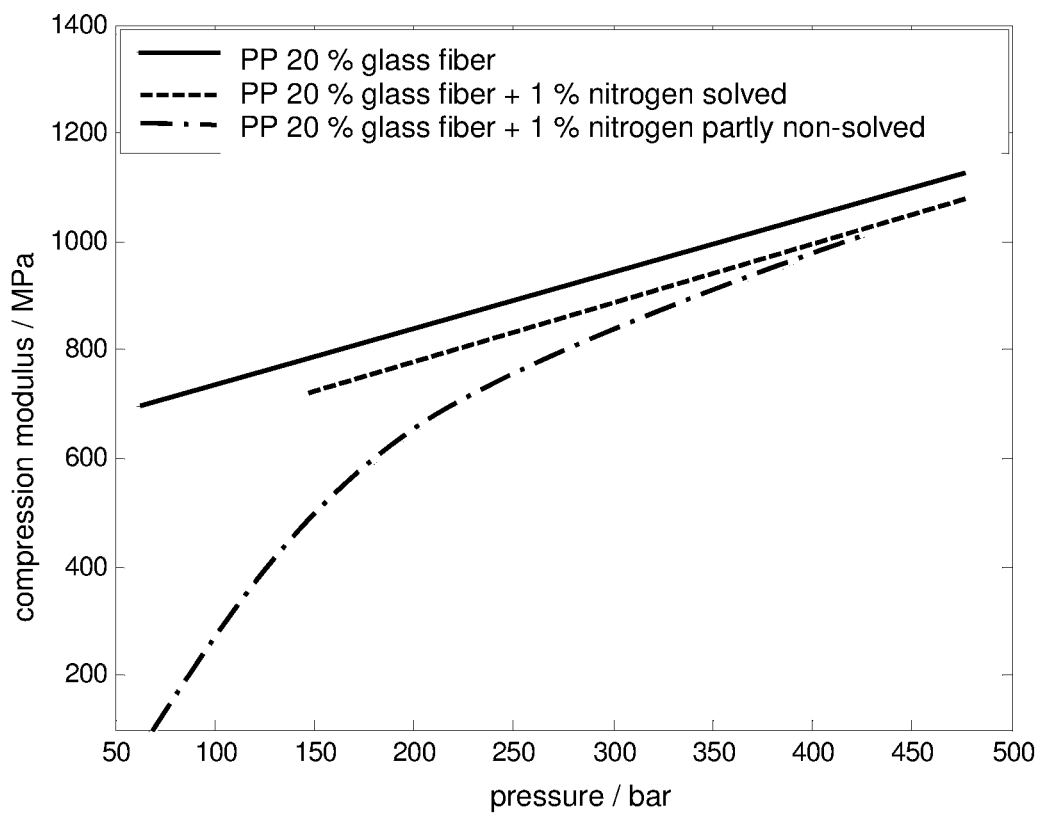

FIG. 5 shows the progress of the injection pressure over the dosing volume during both compression tests from FIG. 4. The value pairs $V_{S1,i}|p_i$ and $V_{S2,i}|p_i$, respectively, are indicated.

Both compression tests are integrated in a single injection cycle at different screw positions. Before the end of the holding pressure phase, the pressure is increased to the desired value (for example, 1000 bar) and then is reduced again to approximately 0 bar (compression test 1). A similar pressure profile is run after the dosing process (hence at a modified dosing volume) (compression test 2). In the example, the value pairs VS2|p are recorded during the decreasing pressure ramp. From these value pairs, the dead volume and the compression volume are determined.

Figure 8:
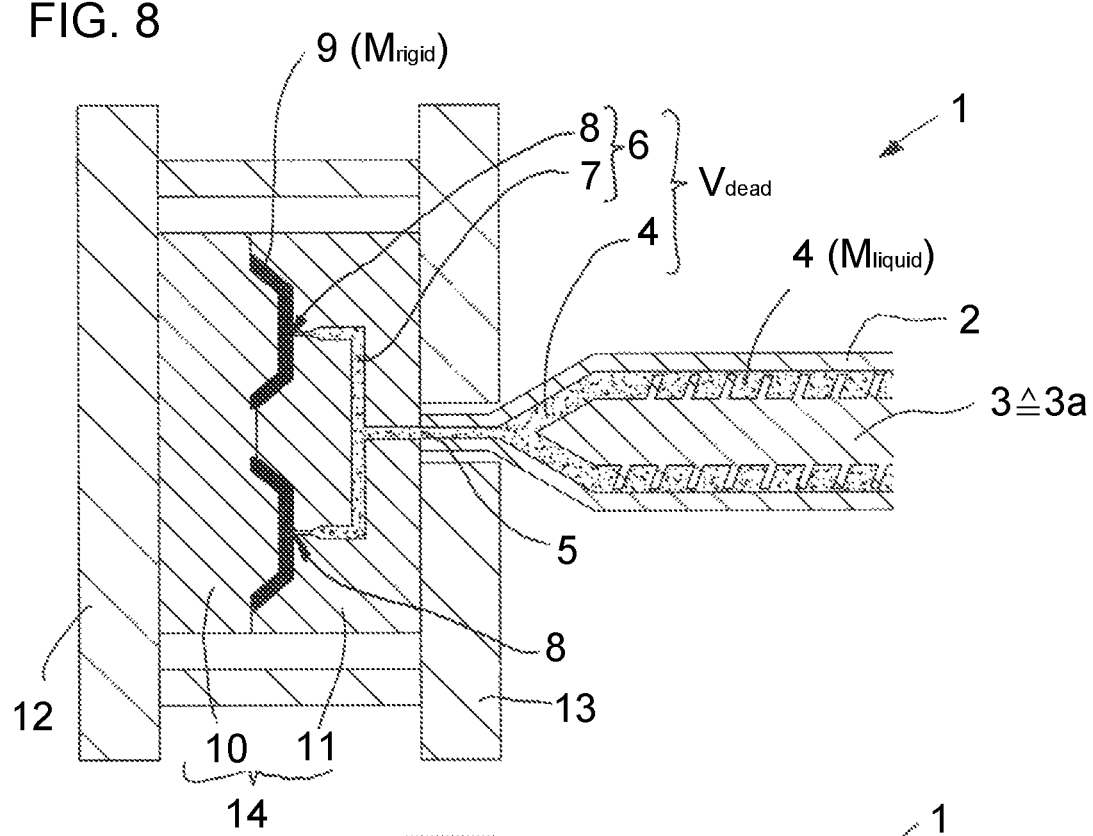
FIGS. 8 and 9 are cross-sectional views schematically showing details of a molding machine.

FIG. 8 shows a molding machine 1 with a hot runner. The material storage space 4 for melted material $M_{liquid}$ or for material to be melted is provided between a plasticizing cylinder 2 and a rotatable, axially movable plasticizing screw 3 which is functioning as a piston 3a. From the nozzle opening 5 in the plasticizing cylinder 2, the material storage space 4 directly merges to the gating system 6. This gating system 6 comprises the distribution system 7 and the gate (i.e., the ingate or inlet port) 8. The gate 8 connects the solidified material $M_{rigid}$ in the mold cavity 9 (also called hollow space) with the distribution system 7. The mold cavity 9 (or the mold cavities 9) is (are) provided between two mold halves 10 and 11 which form the molding tool 14. The mold halves 10 and 11 are each fixed to a mold clamping platen 12 and 13.

Figure 9:
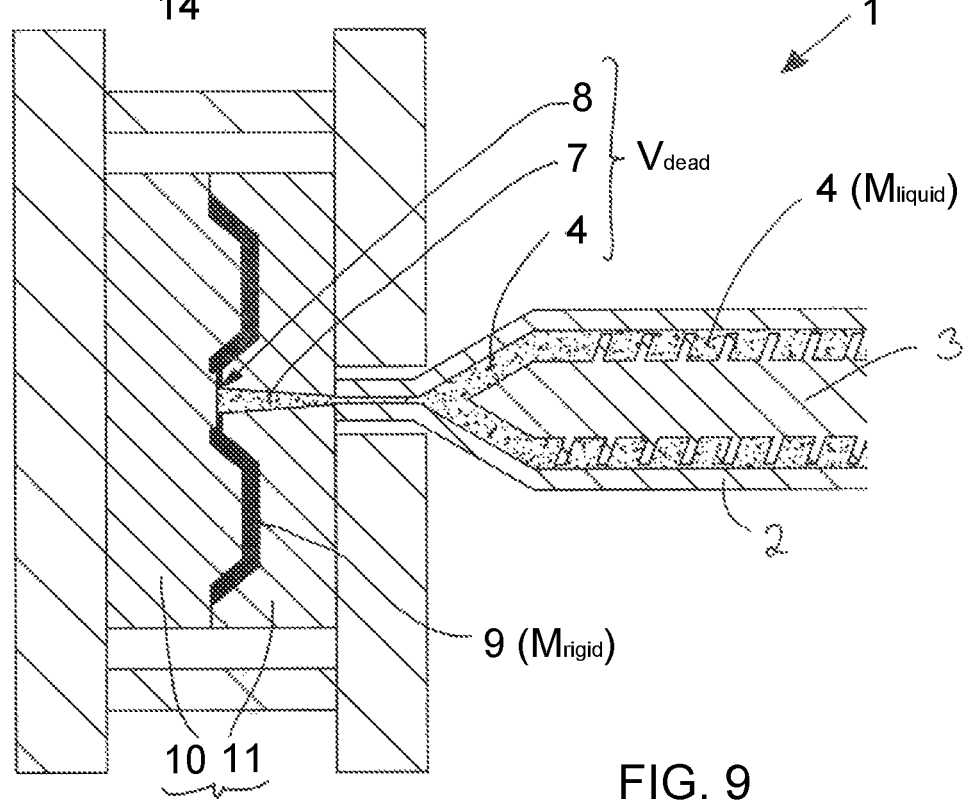

In contrast to FIG. 8, FIG. 9 shows a molding machine 1 with a cold runner. Also here, a parameter for the description of the compression behavior is determined based on the whole dead volume $V_{dead}$ until the gate 8. Also here, the material $M_{rigid}$ of the mold products is solidified in the mold cavity 9, but not the material $M_{liquid}$ in the distribution system 7 (and in the material storage space 4). Thus, the measurement of the compression modulus and of the dead volume $V_{dead}$ includes the non-solidified areas in the molding tool 14. The distribution system 7, formed in FIG. 9 as a so-called sprue bar, contains only melted material $M_{liquid}$ in the schematic illustration. In reality, it is possible that an at least partly solidified boundary layer occurs dependent from the thickness of the distribution system 7 and particularly dependent from the measuring time.

The invention claimed is:
1. A method for determining at least one parameter for a description of a compression behavior of a processed material in a molding machine, said method comprising:
introducing at least a part of the processed material from a material storage space into a mold cavity of a mold via a gating system, the mold cavity being defined by at least two mold portions of the mold, the gating system including a distribution system and an ingate forming an inlet port of the mold cavity, the ingate and at least a portion of the distribution system of the gating system being located within at least one of the mold portions of the mold, the ingate being configured to allow the mold cavity to communicate with the distribution system, wherein the processed material solidifies in the mold cavity;

executing at least one compression test in which (i) a modification of a volume of the material is made and a measurement of a resulting pressure modification is conducted, or (ii) a pressure applied onto the material is modified and a measurement of the resulting modification of the volume of the material is conducted, the material storage space remaining open to the gating system during the at least one compression test; and calculating at least one parameter for the description of the compression behavior based on a result of the at least one compression test by using a mathematical model, wherein the at least one compression test is conducted (i) when the ingate is at least partially solidified or (ii) when a closable hot runner arranged at the ingate is closed, so that a dead volume which extends up to the ingate is considered in said calculating the at least one parameter for the description of the compression behavior.

2. The method according to claim 1, wherein the molding machine comprises a plasticizing screw arranged in a plasticizing cylinder and functioning as a piston, wherein the modification of the volume of the material is effected by modifying a position of the plasticizing screw in the plasticizing cylinder.

3. The method according to claim 1, wherein the molding machine comprises a plasticizing screw arranged in a plasticizing cylinder and functioning as a piston, wherein the modification of the pressure applied onto the material is effected by the plasticizing screw.

4. The method according to claim 1, wherein the molding machine comprises a piston arranged in the material storage space, wherein the modification of the volume of the material is effected by modifying a position of the piston in the material storage space.

5. The method according to claim 1, wherein the molding machine comprises a piston arranged in the material storage space, wherein the modification of the pressure applied onto the material is effected by the piston.

6. The method according to claim 1, wherein the mold having the mold cavity formed therein is provided in a molding tool, wherein the modification of the pressure and/or the volume is effected by a movable molding tool element.

7. The method according to claim 1, wherein at least two compression tests are executed under different boundary conditions.

8. The method according to claim 1, wherein the at least one parameter for the description of the compression behavior is displayed.

9. The method according to claim 1, wherein said executing the at least one compression test is performed independently from a production cycle of the molding machine.

10. The method according to claim 1, wherein said executing the at least one compression test is performed in a production cycle of the molding machine.

11. The method according to claim 10, wherein said executing the at least one compression test is a pressure reduction at an end of a holding pressure phase and/or during a pressure relief before or after a dosing operation.

12. The method according to claim 6, wherein the modification of the pressure and/or the volume is effected by a core pull or an ejector.

13. A method for determining at least one parameter for a description of a compression behavior of a processed material in a molding machine, said method comprising:

introducing at least a part of the processed material from a material storage space into a mold cavity of a mold via a distribution system and an ingate forming an inlet port of the mold cavity, the mold cavity being defined by at least two mold portions of the mold, the ingate and at least a portion of the distribution system being located within at least one of the mold portions of the mold, wherein the processed material solidifies in the mold cavity;

executing at least one compression test in which (i) a modification of a volume of the material is made and a measurement of a resulting pressure modification is conducted, or (ii) a pressure applied onto the material is modified and a measurement of the resulting modification of the volume of the material is conducted, the material storage space remaining open to the distribution system during the at least one compression test; and calculating at least one parameter for the description of the compression behavior based on a result of the at least one compression test by using a mathematical model, wherein the at least one compression test is conducted when (i) the ingate is at least partially solidified or (ii) when a closable hot runner arranged at the ingate is closed, so that a dead volume which extends up to the ingate is considered in said calculating the at least one parameter for the description of the compression behavior.

14. The method according to claim 13, wherein the distribution system comprises the closeable hot runner arranged at the ingate, the closeable hot runner being located within the mold.

* * * * *